United States Patent [19]
Wolber et al.

[11] Patent Number: 5,447,836
[45] Date of Patent: Sep. 5, 1995

[54] BACTERIAL DETECTION BY PHAGE TRANSDUCTION OF ICE NUCLEATION AND OTHER PHENOTYPES

[75] Inventors: Paul K. Wolber, Hayward; Robert L. Green, Berkeley, both of Calif.

[73] Assignee: DNA Plant Technology Corporation, Oakland, Calif.

[21] Appl. No.: 474,282

[22] Filed: Feb. 5, 1990

Related U.S. Application Data

[63] Continuation-in-part of Ser. No. 253,160, Oct. 4, 1988, abandoned.

[51] Int. Cl.$^6$ ............... A23L 3/00
[52] U.S. Cl. ............... 435/4; 435/6; 435/31; 435/39; 435/69.1; 435/170; 435/252.33
[58] Field of Search ............... 435/7.1, 31, 4, 6, 5, 435/34, 39, 172.3, 235, 320, 252.3, 252.33, 252.8, 320.1, 436, 68.1, 69.1, 69.8, 170; 935/9, 27, 31, 58, 72.73

[56] References Cited

U.S. PATENT DOCUMENTS

| | | | |
|---|---|---|---|
| 4,464,473 | 8/1984 | Orser et al. | 435/172.3 |
| 4,650,761 | 3/1987 | Hersgberger et al. | 435/172.3 |
| 4,689,295 | 8/1987 | Taber et al. | 435/6 |
| 4,784,943 | 11/1988 | Warren et al. | 435/7 |
| 4,797,363 | 1/1989 | Teodorescu et al. | 435/235 |
| 4,861,709 | 8/1989 | Ulitzur et al. | 435/6 |

FOREIGN PATENT DOCUMENTS 0168933 1/1986 European Pat. Off. .

OTHER PUBLICATIONS

Joklik, W. K., (1984) Zinsser Microbiology 18th Ed. pp. 447–448.
Makela, Enterobacterial Surface Antigens: Methods for Molecular Characterization, Korhonen et al. eds. Elsevier Science Publ. Amsterdam, pp. 155–178 (1985).
Susskind and Botstein (1978) Microbiol. Rev. 42:385–413 Watanabe et al. (1972) Virol. 50:874–882.
Orbach and Jackson (1982) J. Bacteriol. 149:985–994.
Schmidt and Schmieger (1984) Mol. Gen. Genet. 196:123–128.
Vogel and Schmieger (1986) Mol. Gen. Genet. 205:563–567.
Spanova and Karlovsky (1986) Folia Microbiol. 31:353–363.
Young and Davis (1983) Proc. Natl. Acad. Sci. USA 80:1194–11.
Vieira and Messing (1987) Meths. Enz. 153:3–11.
ASM News (1987) 53:542.
*Molecular Genetics of the Bacterial-Plant Interaction* A. Puhler, ed.,), Elsevier/North Holland Biomedical, pp. 353–361 (1983).
Green et al. (1985) Nature 317:645–648.
Corotto et al. (1986) EMBO J. 5:231–236.
Wolber et al. (1986) Proc. Natl. Acad. Sci. USA 83:7256–7260.
Warren et al. (1986) Nuc. Acids. Res. 14:8047–8060.
G. Vali (1971) J. Atmos. Sci. 28:402–409.
DeVries et al. (1984) Proc. Natl. Acad. Sci. USA 81:6080.
Ludewig (1987) Proc. Natl. Acad. Sci. USA 84:3334.
Chemical and Engineering News, Jan. 23, 1989, p. 18.
Chemical and Engineering News, Jan. 8, 1990, p. 22.

*Primary Examiner*—Christine M. Nucker
*Assistant Examiner*—Laurie Scheiner
*Attorney, Agent, or Firm*—Townsend and Townsend Khourie and Crew

[57] ABSTRACT

Viable bacteria may be detected in biological samples by exposing bacterial cultures obtained from the samples to transducing particles having a known host range. Such transducing particles carry a heterologous gene capable of altering the phenotype of the bacteria in a readily detectable manner. For example, the transducing particles may carry an ice nucleation gene and the alteration of phenotype may be detected using an ice nucleation assay. By employing a panel of phage, unknown bacteria may be typed based on the pattern of reactivity observed. The method is particularly useful for detecting viable bacteria which may have been debilitated by exposure to sterilizing conditions, such as in food processing. The method is also useful for tracking a target bacteria in the ambient environment.

32 Claims, No Drawings

BACTERIAL DETECTION BY PHAGE TRANSDUCTION OF ICE NUCLEATION AND OTHER PHENOTYPES

This application is a continuation-in-part of application Ser. No. 07/253,160, filed on Oct. 4, 1988, now abandoned the disclosure of which is incorporated herein by reference.

BACKGROUND OF THE INVENTION

1. Field of the Invention

The present invention relates generally to the detection and identification of bacteria in biological samples. More particularly, the present invention relates to the screening of biological samples with bacteriophage capable of specifically infecting cells of interest and transforming the infected cells to a detectable phenotype.

The detection and identification of bacterial species and strains is of interest under a variety of circumstances. For example, there is a need to be able to rapidly screen food, water, and other comestibles for contamination with pathogenic bacteria. The detection of bacteria in patient samples is similarly necessary in the treatment of numerous infectious diseases. In the latter case, it is frequently desirable to be able to specifically type the bacteria and would be further desirable to screen the bacteria for sensitivity to various bacteriocides.

Heretofore, various techniques have been used for bacterial identification, including serotyping, nutritional screening, and phage typing. Serotyping utilizes a panel of antibodies capable of binding to distinct cell surface antigens on target bacteria. Based on the observed pattern of binding, the species and strain of the bacteria may be determined. Nutritional screening relies on variations in the metabolic requirements of different types of bacteria. By growing (or attempting to grow) the bacteria on well-defined media, the bacteria may be classified based on those substances which are necessary for growth and those substances which inhibit growth.

Of particular interest to the present invention, bacteriophage have been used to type bacterial cultures based on the limited host range of different phage. By attempting to infect aliquots of a pure culture of unknown bacteria with a panel of different phage, the bacterial cell type can be determined.

While such phage typing is a highly accurate and determinative procedure for identifying bacterial type, it suffers from being both time consuming and labor intensive. Bacteria in a sample must first be grown out so that pure cultures may be isolated. Individual colonies of the pure cultures must then be grown and subsequently divided into aliquots which are exposed to the different phage in the panel. After exposure, conventional plaque assays are run to determine the infectivity of the various phage. The entire procedure takes from 24 to 48 hours, or longer, and requires highly trained personnel for execution. Because of the lengthy procedure, and the need to identify plaques in the bacterial colonies, the procedure is not amenable to automation. Moreover, because of the time required, the procedure is less than ideal for determining the nature of a patient's infection prior to therapy.

Disabled bacteria, such as those debilitated by cooking or partial heat sterilization, are a major detection problem in many food processing situations. Such disabled bacteria frequently remain viable (and thus potentially pathogenic) yet are sufficiently weakened so that detection by conventional assay protocols may require a non-selective recovery step (pre-enrichment) followed by a selective enrichment step to allow growth of the targeted bacteria while growth of competing organisms is inhibited. Such additional steps can significantly add to the time required to perform the assay.

Detection of particular bacteria in open environments, such as air, water, and soil, can also be problematic. Because of the wide variety of species that may be present, it will often be difficult to distinguish a particular species of interest.

In view of the above, it would be desirable to provide improved phage screening assays for detecting and identifying bacterial cells in biological samples. In particular, it would be desirable if such assays could be performed in a relatively short period of time and that the assay protocols be sufficiently simple to be performed by semi-skilled personnel. Preferably, the assays will be performed on mixed cultures, with a minimum number of steps, and result in a detectable event which is easily observed and amenable to automated reading. It would be further desirable if the assays were able to detect partially disabled bacteria which might otherwise require a pre-enrichment step and a selective enrichment step for detection. In addition, it would be desirable to be able to rapidly and conveniently detect particular bacterial cells in open environments, such as air, water, and soil.

2. Description of the Background Art

The use of bacteriophage in characterizing the surface of bacterial cells is discussed in Makela, *Enterobacterial Surface Antigens: Methods for Molecular Characterization*, Korhonen et al., eds., Elsevier Science Publishing, Amsterdam, pp. 155–178 (1985), where conventional plaque assays are employed to determine infectivity of particular phage. The molecular genetics of bacteriophage P22 is discussed in Susskind and Botstein (1978) Microbiol. Rev. 42:385–413. The ability of P22 to act as a transduction vector is described in Watanabe et al. (1972) Virol. 50:874–882 and Orbach and Jackson (1982) J. Bacteriol. 149:985–994. The use of P22 to selectively transduce recombinant plasmids with integrated pac sequences is described in Schmidt and Schmieger (1984) Mol. Gen. Genet. 196:123–128 and Vogel and Schmieger (1986) Mol. Gen. Genet. 205:563–567. Foreign genes are inserted into bacteriophage L (related to P22) by transposon mutagenesis, as described in Spanova and Karlovsky (1986) Folia Microbiol. 31:353–363. The use of λ phage as a cloning vector is described in Young and Davis (1983) Proc. Natl. Acad. Sci. USA 80:1194–1198, where unknown gene products may be detected by antibody probes. The use of M13 phage as a cloning vector is described in Vieira and Messing (1987) Meths. Enz. 153:3–11.

Bacteria may be detected in biological samples by a number of techniques, including selective media, immunoassays, and nucleic acid probes. Particular methods for detecting Salmonella are described in U.S. Pat. No. 4,689,295. A phage-based test for detecting Salmonella in food is described in ASM News (1987) 53:542. The test uses phage to mediate the adsorption of the target Salmonella on a surface.

The ability to nucleate ice formation has been reported to be encoded by a single gene in several ice nucleation-positive (Ina+) bacteria, and this ability can be transferred to *E. coli* by transformation with a plasmid carrying the ice nucleation gene. See, U.S. Pat. No. 4,464,473; Orser et al., *Molecular Genetics of the Bacterial-Plant Interaction* (A. Puhler, ed.), Elsevier/North Holland Biomedical, pp. 353-361 (1983); Green et al. (1985) Nature 317:645-648; and Corotto et al. (1986) EMBO J. 5:231-236. Sequence information for an ice nucleation gene in *P. syringae* (gene inaZ) has been reported; Green et al. (1985) id. The corresponding protein is of approximate molecular weight $1.2 \times 10^5$. Sequence information for an ice nucleation gene in *P. fluorescens* (gene inaW) has also been reported. See, Warren et al. (1986) Nuc. Acids. Res. 14:8047-8060. Information concerning the identification and purification of the inaZ and inaW proteins is reported in Wolber et al. (1986) Proc. Natl. Acad. Sci. USA 83:7256-7260.

The droplet freezing assay is a known method of testing for the presence of whole cell ice nucleating bacteria and cell-free nuclei. The method consists of laying out an array of N droplets of volume V (usually 0.01 ml) on a nucleus-free surface, cooling to temperature T (less than 0° C.) and scoring $N_f$, the number of droplets frozen. The number of nuclei/ml is then calculated by the following formula: nuclei/ml $= (1/V) \log_e [N/(N-N_f)]$. G. Vali (1971) J. Atmos. Sci. 28:402-409.

SUMMARY OF THE INVENTION

According to the present invention, methods and compositions are provided for detecting and identifying viable bacteria in biological samples. For these purposes, the term viable bacteria includes all bacteria capable of expressing genes (transiently or otherwise). The compositions comprise bacteriophage particles capable of infecting a known host range of bacteria and transducing such bacteria to a readily detectable phenotype, preferably an ice nucleation phenotype. The method of the present invention is suitable for detecting most types of bacteria, with the limitation that the target bacteria must be susceptible to bacteriophage infection and the wild-type bacteria cannot itself produce the detectable phenotype. Biological samples of interest may be obtained from virtually any source capable of supporting or preserving bacteria in a viable condition, including patient specimens, water, dairy products, meat products, and the like. Such samples will often contain mixed or impure populations of bacteria, possibly but not necessarily containing a target bacterial species of interest. The method is particularly useful with samples that have been subjected to sterilization, where the object is to detect viable bacteria which survived such sterilization. Use of the transducing particle assays of the present invention is capable of detecting partially debilitated (but viable) bacteria which may be present after sterilization. A preferred method of the present invention is the detection of Salmonella, particularly in food which has undergone sterilization.

The method of the present invention may be used either for screening samples for the presence of bacteria or for typing bacteria of an unknown strain or species. For screening, only a single bacteriophage having a relatively broad host range will be necessary. The biological sample is incubated under conditions suitable for promoting the growth of bacteria, and there is no need to provide a pure culture. Such screening procedures are very rapid and simple and are particularly useful in identifying contaminated samples, such as food or water samples. Bacterial typing, in contrast, utilizes a panel of bacteriophage having distinct or overlapping host ranges. Each of the bacteriophage is tested against a culture (pure or otherwise) of the bacteria, typically by adding various members of the phage panel to aliquots of the culture to be tested. The type of bacteria is then determined based on the pattern of reactivity of the individual bacteriophage. Although typing may involve the use of a pure culture of the bacteria, the method of the present invention has the advantage that the detection of phage infectivity is very rapid, greatly shortening the overall time required for the assay. Moreover, the detectable phenotype, such as ice nucleation, may readily be detected by automated systems, reducing the labor required for the assay.

The method of the present invention will also find use in following or tracking a modified bacteria which has been released in an environment, typically the ambient environment. The bacteria are first modified to express a cell surface marker recognized by a transducing particle. Bacterial samples from the environment may then be screened with the transducing particle which is capable of conferring a detectable phenotype. The ice nucleation phenotype is particularly preferred because of its sensitivity of detection and low background level in most environments.

The method of the invention takes advantage of the specificity of bacteriophage for particular bacteria. This specificity is retained when the bacteriophage are modified to contain a marker gene (see Example 5). As a consequence, detection via the assay of the invention can be accomplished on a specific basis, irrespective of the presence of other (non-target bacteria). Of course, it is possible (although unlikely) that the modified bacteriophage of the present invention may have some change in their host range specificity when compared to the wild type phage from which they have derived. Such variation will not be a problem so long as the bacteriophage retains specificity for the bacteria of interest and is free from specificity for other bacteria which might be present in a particular sample.

An important advantage of the method of the invention is that it may be used in assays involving bacterial cells which are viable but disabled (physiologically compromised) in some fashion, e.g., by exposure to injurious or debilitating treatments such as heat, cold or desiccation. Such disablement commonly results during industrial processing, e.g., processing of food-borne bacterial contaminants. The assay of the invention is capable of detecting disabled cells (see Example 4, involving heat disabled Salmonella cells), including disabled cells in a mixture of healthy and disabled cells. This provides an important time-saving feature in that it minimizes or eliminates the need for a pre-enrichment step and a selective enrichment step. Such steps are commonly used in other bacterial assays as a means to allow the target cells to multiply to a detectable level while the populations of other organisms are kept in check. See Andrews, *Injured Index and Pathogenic Bacteria*, CRC Press, Boca Raton, Fla, pp. 56-113 (1989). Because debilitated cells may be unable to survive the rigors of selective enrichment, a prior nonselective "pre-enrichment" step is often employed to allow the weakened cells to stabilize. The FDA Salmonella isolation protocol recommends a minimum of 22 hours for each of the two steps (pre-enrichment and selective enrichment); Andrews et al., *Bacteriological Analytical Manual*, 5th Edition, Food and Drug Administration, District of Columbia, Chapter VI, 1-29 (1978). The method of the invention thus offers considerable time saving advantages when applied to systems having disabled cells.

In a preferred embodiment, the transducing phage carries an ice nucleation gene. The sample is first incubated with the phage under conditions which promote attachment of the phage to the cell, typically at a temperature in the range from about 35° C. to 40° C. without agitation for a time in the range for about 15 to 120 minutes. Thereafter, the sample is incubated in a suspension under conditions which promote development of the ice nucleation phenotype, typically at a temperature in the range from about 20° C. to 25° C. for a period in the range from about 30 minutes to 2 hours. Bacteria transformed to the ice nucleation phenotype are detected by a conventional cryoassay, typically by dividing the suspension to be tested into droplets having volumes below about 10 μl and exposing the droplets to a temperature in the range from about −3° C. to −12° C., more usually in the range from about −8° C. to −10° C. The formation of ice nuclei in such a temperature range indicates the presence of ice nucleation sites on the cell surfaces of the bacteria.

A particular advantage of the ice nucleation phenotype is that target bacteria may be detected at very low levels, even in the presence of a large excess of viable or non-viable non-target bacteria. Moreover, the sensitivity of the detection method of the ice nucleation assay of the present invention may be increased by decreasing the temperature at which the ice formation is observed. At lower temperatures, fewer ice nucleation positive bacteria are required to cause observable ice nucleation. The formation of ice nuclei resulting from the presence of ice nucleation positive bacteria is a very rapid phenomenon, allowing very rapid assay methods. Finally, the ice nucleation phenotype is extremely rare in nature, allowing assays having very low backgrounds.

DESCRIPTION OF THE SPECIFIC EMBODIMENTS

The present invention utilizes modified bacteriophage, referred to hereinafter as transducing particles, in order to detect or identify bacterial cells in biological samples. As used herein, the term transducing particles shall also include component parts of a modified bacteriophage which component parts, when mixed together under proper conditions, will combine to form the modified bacteriophage. The biological samples may be virtually any substance or medium capable of supporting bacterial growth or otherwise suspending bacterial cells in a viable state. Biological samples of particular interest to the present invention include water, soil, food samples, such as meat products and dairy products which are particularly susceptible to bacterial contamination, patient samples, such as blood, plasma, serum, sputum, semen, saliva, lavage, feces, cell culture, and the like.

The range of bacterial cells to be detected is limited only by host ranges of available bacteriophage. Of particular interest are pathogenic bacteria which are capable of contaminating food and water supplies and are responsible for causing diseases in animals and man. Such pathogenic bacteria will usually be gram-negative, although the detection and identification of gram-positive bacteria is also a part of the present invention. A representative list of bacterial hosts of particular interest together with the diseases caused by such hosts and the bacteriophage capable of infecting such hosts is presented in Table 1.

TABLE 1

| Bacteria | Gram type | Diseases Caused | Bacteriophage |
|---|---|---|---|
| Bordetella pertussis | negative | whooping cough | See, N.A. Pereversev et al. (1981) Zh. Mikrobiol. 5:54–57 |
| Brucella abortus | negative | brucellosis | TB; 212; 371 |
| Mycobacterium tuberculosis | — | tuberculosis | LG; DSGA |
| Salmonella typhi | negative | typhoid fever | 163; 175; ViI; ViVI; 8; 23; 25; 46; 175; F0 |
| Salmonella typhimurium | negative | gastroenteritis; septicemia | L; P22; 102; F0 |
| Salmonella schottmulleri | negative | gastroenteritis; septicemia | 31; 102; F0; 14 |
| Salmonella cholerae suis | negative | gastroenteritis; septicemia | 102 |
| Salmonella anatum | negative | gastroenteritis; septicemia | E15 |
| Salmonella newington | negative | gastroenteritis; septicemia | E34 |
| Samonella bovismorbificans | negative | gastroenteritis; septicemia | 98 |
| Serratia marcescens | negative | wound infections | S24VA |
| Shigella dysenteriae | negative | bacterial dysentery | φ80; P2; 2; 37 |
| Staphylococcus aureus | positive | toxic shock, infections | K; P1; P14; UC18; 15; 17; 29; 42D; 47; 52; 53; 79; 80; 81; 83A; 92 |
| Streptococcus pyogenes | positive | streptococcal infections | φX240; 1A; 1B; 12/12; 113; 120; 124 |
| Vibrio cholerae | negative | cholera | 138; 145; 149; 163 |
| Yersinia pestis | negative | plague | R; Y; P1 |
| Listeria monocytogenes | positive | meningitis, abcess | 243 |
| Pseudomonas aeruginosa | negative | wound and burn infection | B3; pp. 7 |
| Escherichia coli | negative | urinary infection | P1; T3; T4; T7 |
| Klebsiella pneumoniae | negative | respiratory, urinary infection | 60; 92 |

The transducing particles of the present invention are obtained by modifying a naturally-occurring bacteriophage to carry a gene capable of transforming the target bacteria to an easily recognizable phenotype, referred to hereinafter as the primary marker gene. The transducing particle must be capable of specifically introducing the primary marker gene into the target bacterial host in such a way that the bacterial host can express the gene function in a detectable manner. A large number of bacteriophage exist and may be selected for modification based on the desired host range and the ability of the bacteriophage to carry and transduce the gene of interest. In particular, the bacteriophage must be large enough to accomodate the primary marker gene, associated promoter region, and any other DNA regions which may be included. Modified bacteriophage of the present invention will usually retain the normal host range specificity of the unmodified bacteriophage, although some alteration in specificity would be acceptable so long as it does not affect the ability to identify the selected target bacteria.

The bacteriophage to be modified may be temperate or virulent, preferably being temperate in order to provide prolonged expression of the primary marker gene in the target bacteria. Alternatively, modification of the bacteriophage may result in a defective transducing particle which is capable of introducing the marker gene into a target bacterial host, but which is incapable of achieving lytic or lysogenic infection. In the latter case, the primary marker gene may be part of a plasmid or other self-replicating episomal unit which will be sustained and expressed in the infected host.

Transduction of the marker phenotype may take place via transient expression (i.e., expression from a gene which is not stably inherited by the cell) of the marker gene. In such case, the DNA transduced by the bacteriophage may not survive intact through the entire test period. However, transcription of the marker gene transduced by the phage will be sufficiently efficient before the DNA is degraded to ensure that the bacteria has assembled a functional marker by the end of the test period. The bacteria can thus be detected by the assay of the invention even if the bacteria degrades the phage DNA.

Bacteriophage useful in the present invention may be obtained from microbiological repositories, such as the American Type Culture Collection, 12301 Parklawn Drive, Rockville, Md. 20852. Virulent bacteriophage are available as bacteria-free lysates, while lysogenic bacteriophage are generally available as infected host cells.

Wild-type bacteriophage obtained from any source may be modified by conventional recombinant DNA techniques in order to introduce a desired primary marker gene capable of producing the detectable phenotype of interest. Prior to introduction, the marker gene of interest will be combined with a promoter region on a suitable gene cassette. The gene cassette may be constructed by conventional recombinant DNA techniques in a suitable host, such as E. coli. Both the marker gene and the promoter region should be chosen to function in the target host, and the cassette may optionally include a second marker gene, such as antibiotic resistance, heavy metal resistance, or the like, to facilitate in vitro manipulation.

The primary marker gene (or genes, if not a single gene system) should be capable of expressing a screenable phenotype in the target bacterial host. As used hereinafter and in the claims, the phrase screenable phenotype is intended to mean a characteristic or trait which allows cells which express the phenotype to be distinguished from other cells which do not express the phenotype, even when all cells are growing and reproducing normally in a mixed culture. That is, detection of the characteristic or trait may be carried out while the infected target cells are present in mixed population of viable, usually proliferating non-target bacteria which do not express the phenotype. Preferably, the screenable phenotype will comprise a visually observable trait, i.e., one that can be directly or indirectly observed in a mixed population of target and non-target cells. The phenotype will usually not be selectable, i.e., one which provides for survival or preferential growth under particular conditions (positive selection) or which provides for growth inhibition or killing under particular conditions. The method of the present invention does not require that target bacteria present in the sample be isolated from or enriched relative to non-target bacteria which may be present in the sample because the trait will be observable when target bacteria comprise only a portion of the viable bacteria present.

Suitable screenable phenotypes include bioluminescence, fluorescence, enzyme-catalyzed color production (e.g., using the enzyme β glucuronidase (GUS)), ice nucleation activity, and the like. Each of these phenotypes may be observed by conventional visualization techniques which provide the chemical reagents necessary to complete a signal producing reaction. Preferred is the use of ice nucleation activity which is demonstrated herein to be easily and rapidly detectable using conventional ice nucleation assays. While the remainder of this disclosure is directed primarily at the preferred introduction and detection of ice nucleation activity and target bacterial cells, certain aspects of the present invention may be achieved with other detectable phenotypes.

Suitable ice nucleation genes may be isolated from microorganisms which naturally display an ice nucleation phenotype. Exemplary ice nucleation genes and the bacteria from which they may be isolated include inaZ isolated from Pseudomonas syringae S203, inaY isolated from Pseudomonas syringae PS31, inaW isolated from P. fluorescens MS1650, and iceE isolated from Erwinia herbicola. The sequence of inaZ is given in Green and Warren (1985) Nature 317:645-648, while the sequence of inaW is given in Warren et al. (1986) Nucl. Acid. Res. 14:8047-8060, the disclosures of which are incorporated herein by reference. See also U.S. Pat. No. 4,464,473, the disclosure of which is incorporated herein by reference. The teachings of these references are sufficient to enable one skilled in the art to isolated an ice nucleating organism from the wild and obtain an ina gene therefrom by conventional cloning and screening techniques.

The transducing particles of the present invention may be prepared by a number of conventional genetic manipulation techniques, including site-directed insertion of the marker gene cassette into the bacteriophage genome, packaging of the plasmid carrying the marker gene or a portion thereof into the bacteriophage coat, transposon mutagenesis, and homologous recombination. The choice among these alternatives depends on the nature of the bacterial host, the nature of the bacteriophage, and the extent to which the bacteriophage has been characterized.

For well characterized bacteriophage, particularly those which have been genetically mapped, it is frequently desirable to place the primary marker gene cassette, including the promoter region and optionally the second marker, into the bacteriophage genome by standard recombinant DNA techniques. After preparing the plasmid in a suitable host as described above, the marker gene cassette is excised and inserted into the desired bacteriophage. Strategies for insertion into λ phage, which may be generalized to other bacteriophage, are described in Young and Davis (1983) Proc. Natl. Acad. Sci. USA 80:1194-1198, the disclosure of which is incorporated herein by reference.

Transducing particles capable of lytic or lysogenic infection are prepared by deletion of nonessential regions of the bacteriophage genome and substitution of the gene cassette. Desirably, the regions deleted and inserted will be approximately the same size so that the packaging may be effected with minimum disruption. In some cases, however, it may be necessary to delete certain essential regions of the bacteriophage genome, particularly when it is desired to insert relatively large marker gene cassettes. In that case, the transducing particles will retain the ability to insert the DNA into the desired bacterial host, but will be unable to reproduce within the host. Reproduction may be obtained, however, by providing a helper bacteriophage, such as the wild-type bacteriophage, which is able to provide essential packaging functions.

Alternatively, for well characterized bacteriophage, it is possible to package the plasmid or the marker gene cassette by attachment of the bacteriophage pac site in a DNA construct with the plasmid or cassette. The pac site may be obtained from the bacteriophage genome and cloned into the plasmid carrying the primary marker gene, promoter region, and optional second marker. The plasmid may then be transferred to a suitable bacterial host which is then infected with a bacteriophage having a defective pac site. The bacterial host will then produce transducing particles having the plasmid and/or marker gene cassette packaged within a bacteriophage coat capable of inserting the plasmid DNA into bacteria of its host range. General methods for cloning pac sites and producing packaging-deficient bacteriophage are described by Vogel and Schmieger (1986) Mol. Gen. Genet. 205:563–567, the disclosure of which is incorporated herein by reference.

For less characterized bacteriophage, transposon mutagenesis may be employed to prepare the transducing particles of the present invention. The method of Spanova and Karlovsky (1986) Folia Microbiol. 31:353–363 for the mutagenesis of phage L (Salmonella typhimurium), the disclosure of which is incorporated herein by reference, may be generalized to apply to other transposons, bacteriophage, and bacterial hosts. A marker gene cassette from the plasmid, as described above, is first inserted into a desired transposon by conventional techniques. The modified transposon is then transposed into the desired bacteriophage by simultaneous infection of a suitable host with both the modified transposon and the bacteriophage. The host cells are then incubated until lysis occurs, and the released phage are collected. A fraction of the released phage will be carrying the transposon insert. Host cells free from bacteriophage are then infected with the phage mixture obtained as described above, and cells carrying a detectable marker present on the transposon selected. Unlysed selected cells, in which the bacteriophage carrying the modified transposon has become lysogenic, are then plated on selective media and screened for the desired phenotype. Such selected cells thus contain prophage having the desired primary marker gene under the control of a suitable promoter. Transducing particles may then be obtained by inducing the prophage to a lytic state, which results in cell lysis and release of a large quantity of suitable transducing particles.

The use of a secondary selection marker in the preparation of transducing particles by transposon mutagenesis is helpful, but not required. Phage which have been mutagenized to carry the primary selection marker, for example the ice nucleation gene, may be identified over the background of wild-type phage by performing an appropriate assay, such as a replica plating assay for ice nuclei in the case of the ice nucleation gene. Such screening assays are taught in Lindow et al. (1978) App. Environ. Microbiol. 36:831–838, the disclosure of which is incorporated herein by reference.

In addition to the above techniques, transducing particles may be prepared by homologous recombination resulting in low frequency transducing particles or high frequency transducing particles. Low frequency transducing particles may be constructed from the plasmid carrying the marker gene cassette by first preparing a restriction library of the bacteriophage genome of interest. The restriction fragments from the library are then cloned into the plasmid in a suitable host, resulting in plasmids carrying relatively large regions homologous with the wild-type bacteriophage. Such regions serve as cross-over points in homologous recombination events in a manner well described in the art. The recombinant plasmid is then introduced to a suitable bacterial host, and colonies which express the primary or secondary marker gene are selected for infection with the wild-type bacteriophage. A relatively low percentage of the transducing particles produced by the bacteriophage infection will include the entire plasmid carrying the marker gene cassette as an insert. A fresh bacterial culture is then infected with the mixed transducing particles, and transformed colonies are selected based on the expression of either the primary marker or secondary marker carried by the plasmid.

A specific example of the preparation of low frequency transducing particles capable of specifically infecting S. typhimurium is given in the Experimental section hereinafter as Example 2.

Low frequency transducing particles having a relatively high transduction frequency, usually greater than about 5%, may be used for performing the assay of the present invention. For transducing particles having a lower rate of transduction, it will usually be desirable to further modify the bacterial hosts to produce high frequency transducing particles.

High frequency transducing particles are prepared as described above, but employing a prophage in the bacterial genome as the target for homologous recombination. To this end, a lysogenic strain (a strain carrying the wild-type bacteriophage DNA in its genome as a prophage) is employed and transformed with a plasmid carrying the gene marker cassette which is incapable of replication in the host. Thus, only hosts where the selective markers have been incorporated in the prophage will be viable under the appropriate selective conditions. Alternatively, the plasmid may be otherwise altered so that recombination with the prophage is readily detected. Plasmids incapable of replicating in the desired bacterial host may be prepared by several techniques. For example, low frequency transducing phage prepared as described above may be utilized as the immunity functions expressed by the prophage will prevent replication. Second, plasmids capable of replication in a suitable cloning host but incapable of replication in the target host of interest may be used. Finally, the plasmid may be modified so that the primary marker gene is inserted into the prophage, while the secondary marker is placed outside the region which is incorporated in the prophage. Recombination may then be detected by screening for cells which express the primary selection phenotype, but which have lost the secondary selection phenotype. Incorporation of the desired marker gene into the prophage may be confirmed by standard techniques, such as Southern blotting as described in Southern (1975) J. Molec. Biol. 98:503–517.

A specific example of a high frequency transducing particle capable of specifically infecting S. typhimurium is given in the Experimental section hereinafter as Example 3.

A preferred means of making a high frequency transducing particle via homologous recombination involves the use of transposon tagging where an insertable element comprises the gene for a detectable phenotype of interest joined to the essential terminal sequences of a transposon. Such insertable elements will be able to identify sites in a bacteriophage genome into which an ice nucleation or other reporter gene can be inserted without interfering with essential bacteriophage functions. In general, any bacterial transposon can be used to prepare the insertable element. It is desirable that the size of the resulting insertable element be as small as possible to allow packaging of the entire resulting phase genome into mature viral particles.

As the frequency of occurrence of suitable sites in transposon tagging is expected to be low, the bacterial transposon used preferably encodes functions that allow for the selection of transposition events. To this end, a naturally occurring transposon may be modified to provide a small-sized, selectable transposon. Any transposon in which the transposase functions can be separated from the ends of the transposable element would be suitable. These include but are not limited to IS (insertion sequence) elements, such as IS50, and transposable drug resistance elements, such as Tn3, Tn5, and Tn7, as is known in the art. The bacterial transposon Tn5 is most convenient for such modifications as it has been characterized in great detail in the art. Krebs and Reznikoff, (1986) J. Mol. Biol. 192:721-791; Dodson and Berg, (1989) Gene 76:207-213.

As one approach, the essential terminal DNA sequences of a transposon can be synthesized chemically by methods known in the art. In synthesizing these DNA sequences, it is advantageous to include flanking sequences (polylinkers) that contain the recognition sites for a number of restriction endonucleases. This facilitates the insertion of selectable markers between the ends of the transposon element, and allows the element thus created to be easily cloned into a vector plasmid, the choice of which depends on the nature of bacterial host for the particular bacteriophage. As is well known in the art, narrow host range plasmids derived from ColE1, P15A, or pMB9 replicons (such as pAT273, pACYC184, pBR322, or pUC19) would be suitable for use in bacteria from the family Enterbacteriaceae, while in general, any broad host range plasmid derived from the incompatability groups IncP, IncW or IncQ (such as those derived from pRK2, pS-a or pRSF1010) would be suitable for use in other gram negative bacteria. For gram positive bacteria other suitable plasmid vectors known in the art can be used.

It is preferred that the transposase for the chosen transposon not be located between the ends of the transposon. In this way, once the transposable element has been inserted in the bacteriophage genome, it will be unable to undergo a second transposition event. In general, it is also desirable that this location be on the same DNA molecule as the element to be transported (i.e., in cis), although the transposon and the transposase could, in some systems, be located on separate plasmid replicons (i.e., in trans).

It may also be desirable to modify the expression of the transposase gene of the transposable element by inserting the coding sequence for the transposase protein downstream of a highly expressing bacterial promoter. Such promoters are known to those of skill in the art, and include the tac, trc and lac promoters of $E.$ $coli.$ It is known that overexpression of bacterial transposases can be deleterious to the host cell, so it is also desirable that the transcription from the chosen promoter be capable of regulation. Promoters such as the tac, trc and lac promoters are repressed by the lac repressor, the product of the lacI gene. Inclusion of such a gene on the same molecule as the transposase will ensure expression of the transposase protein only under conditions in which repression is eliminated (i.e., inducing conditions). For the lacI gene, the chemical isopropylthiogalactoside (IPTG) tends to be lac repressor limiting.

In general, any combination of a highly expressing yet repressible promoter and its associated repressor gene will function to give the same result. If a selectable marker is used as an insert between the ends of the transposable element, the marker should be as small as possible. It is preferred that the size of the transposable element be less than 1 kilobase. In general, antibiotic resistance genes are larger than is desirable, although the absolute size of the transposed DNA is determined by the packaging limits of the individual bacteriophage.

A preferred means of selection uses the phenomenon of α-complementation to lactose utilization as described in $E.$ $coli.$ Here, a small fragment of the β-galactosidase gene (the lacZ α fragment which is approximately 500 base pairs in length) encodes a polypeptide which restores functionality to another mutant polypeptide in which amino acids have been deleted (the M15 deletion). The inclusion of the lacZ α fragment between the ends of the transposon allows for the selection of bacteriophage carrying the inserted DNA by their ability to restore lactose utilization to host bacteria which carry the lacZM15 deletion either on a plasmid or in the chromosome. The DNA fragments encoding these two activities have been characterized in detail and can be readily manipulated by those skilled in the art. See, I. Zabin et al., The Operon (eds. J. H. Miller et al.), Cold Spring Harbor Laboratory (New York), 104-107 (1978).

A plasmid containing the transposase, end piece DNA, marker DNA and repressor, as described above, is introduced into a bacterial cell (e.g., Salmonella) containing within the bacterial genome prophage DNA (e.g., P22). The transposase is induced by an appropriate chemical inducer (e.g., IPTG) and the bacterial cells are grown for a number of generations. The prophage is then induced, e.g., with an appropriate chemical inducer (e.g., mitomycin C) yielding bacteriophage. The bacteriophage which carry a transposon insertion are selected by infecting a suitable bacterial host (e.g., carrying M15 deletion) with the induced phage lysate. Infected cells are plated out on media selective for the marker (e.g., lacZ α), resulting in selection of cells containing a prophage genome which in turn contains the transposon fragment containing end pieces and marker. The selected cells are then induced for phage lysis to obtain pure phage preparations. The DNA fragment of bacteriophage carrying the transposon insertion is isolated using in vitro techniques. This fragment is cloned on a suitable plasmid vector. The ice gene is then substituted for the selectable marker (e.g., lacZ α) using in vitro techniques. Homologous recombination can then be carried out using a plasmid containing the ice gene so prepared, where the homologous recombination involves recombination between prophage DNA in the bacterial genome and prophage DNA flanking the ice gene on the plasmid. The resultant strain, upon phage induction, yields transducing particles containing ice gene DNA at a site within the prophage DNA where the presence of the ice gene at that site does not disrupt essential phage functions.

Transducing particles prepared as described above are used to detect target bacteria in biological samples as follows. In some instances it will be possible to infect a biological sample and observe the alteration and phenotype directly, although in other cases it may be preferred to first prepare a mass culture of the bacteria present in the sample. Methods for obtaining samples and (if necessary) preparing mass culture will vary depending on the nature of the biological sample, and suitable techniques for preparing various sample types are described in detail in standard microbiology and bacteriology texts such as Bergey's Manual of Determinative Bacteriology (8th ed.), Buchanan and Gibbons (eds.) Williams & Wilkens Co., Baltimore (1974); Manual of Methods for General Bacteriology, Gerhardt et al. (eds.), Am. Soc. Microbiology, Washington (1981); and Manual of Clinical Microbiology (2nd ed.), Lennette et al. (eds.), Am. Soc. Microbiology, Washington (1974).

Once the biological sample has been prepared (with or without growth of a mass culture), it will typically be exposed to transducing particles under conditions which promote binding of the particles to the bacteria and injection of the genetic material, typically at a temperature which supports rapid growth of the bacteria (e.g., 35° C. to 40° C.) without agitation for a time sufficient to allow infection (e.g., 15 minutes to 120 minutes). For transducing particles carrying an ice nucleation gene, the sample is then incubated at a lower temperature (e.g., 20° C. to 25° C.) to permit formation of ice nucelation sites. After a short time, typically 30 minutes to 2 hours, the sample may be assayed for ice nuclei as described in more detail below.

For transducing particles carrying an ice nucleation gene, conventional droplet freezing assays as described in Vali (1971), supra., may be useful to detect transformation to the ice nucleation phenotype. Alternatively, a specific fluorescence freezing assay for detecting the ice nucleation phenotype is taught in U.S. Pat. No. 4,784,943, the disclosure of which is incorporated herein by reference. Briefly, the assay for detecting ice nucleation comprises use of fluorescent compounds which in aqueous state manifest a change in fluorescence or visible properties upon freezing or thawing of the aqueous medium. Suitable fluorescent compounds may be selected from the fluorescein family, e.g., calcein, carboxyfluorescein, and related compounds.

The method of the present invention will be used most frequently to screen for a specific type of bacteria (as determined by the host range of the transducing particle) in a mixed population of bacteria derived from a biological sample as described above. The mixed bacterial populations need not be selected prior to screening. Preparation of the sample prior to screening will generally not provide a homogeneous bacterial population, although it is possible to combine the screen of the present application with nutritional selection as described below.

In contrast to conventional phage transduction techniques intended to produce homogeneous colonies of transduced bacterial cells, the method of the present invention does not require that the transduced bacteria be isolated in any way. Instead, the screenable phenotype, e.g., a visually observable trait, conferred by the primary marker gene can be detected in a non-selected portion of the biological sample where viable, usually proliferating, non-target bacteria will be present. The screening can occur without selection since there is no need to isolate the transduced bacteria.

As described above, the assay of the present invention is useful for screening biological samples to determine whether bacteria present in the host range of the transducing particle are present. The present invention is also useful for typing bacterial species and strains in a manner similar to conventional phage typing which instead relies on much slower plaque assays for determining phage infection.

For typing according to the present invention, a panel of transforming particles having differing, usually overlapping, host ranges are employed. The species and strain of the target bacteria (usually present in a substantially pure culture) may then be determined based on the pattern of reactivity with the various transforming particles. Often, such tests may be run on a single carrier, where the different transforming particles are spotted in a fixed geometry or matrix on the carrier surface. The pattern of reactivity may then be rapidly observed. In contrast to the previously-described screening methods, these typing methods will be useful in characterizing homogeneous bacterial cultures (i.e., contained on a single species or strain) as well as typing target bacteria in mixed populations.

The present invention may be combined with nutritional screening in order to further characterize the bacteria being investigated. By providing a selective medium during either the mass culture or the plating culture, the range of bacteria which can remain viable may be limited. As the phenotypic assay of the present invention can only detect viable cells, absence of a detectable phenotype limits the type of bacteria which may be present. By properly combining the host range of the transducing particles and the viability range of the selective medium, the method of the present invention can be made very specific for the type of bacteria being determined.

A second approach for increasing the ability of the present invention to specifically identify bacterial hosts involves the use of immunoadsorption. Immobilized antibodies, including antisera or monoclonal antibodies, are utilized to specifically capture bacterial cells based on the identity of their cell surface epitopes. The bacteria may then be further detected using the transducing particles of the present invention, as described above. Suitable materials and methods for the immunoadsorption of particular bacterial species and strains on solid phase surfaces are described in Enterobacterial Surface Antigens: Methods for Molecular Characterization, Korhonen et al. (eds.), Elsevier Science Publishers, Amsterdam (1985).

The present invention can be particularly useful in patient diagnosis as it allows the determination of bacterial sensitivity to antibiotics and other bactericides. By performing a short incubation of the bacteria with an antibiotic or bactericide to be screened prior to exposure to the transducing particles of the present invention, the metabolic activities of the cells will be halted and the alteration of phenotype prevented. Such testing will be useful after the presence of the bacteria is initially confirmed using the transforming particles as described above. Antibiotics and bactericides which are determined to be lethal to the bacterial infection may then be employed for treatment of the patient. Such rapid and early detection of useful antibiotics and bactericides can be invaluable in treating severe bacterial infections.

In a specific embodiment, a means is provided for assaying bacteria which have been previously rendered susceptible to bacteriophage of the invention on a phagespecific basis. That is, in a first step, the target bacteria are modified, e.g., by transformation, so that they contain or express a cell-specific receptor for the bacteriophage of interest. In a second step, the modified (or tagged) bacteria are introduced into, or mixed into, a sample environment in which they are to be followed. The sample environment can be any setting where bacteria exist, including outdoors (e.g., soil, air or water); on living hosts (e.g., plants, animals, insects); on equipment (e.g., manufacturing, processing or packaging equipment); and in clinical samples. The bacteriophage assay of the invention (as described previously) can then be carried out, using bacteriophage specific for the introduced receptor, and the presence of the tagged bacteria can be monitored or quantified.

An advantage of this embodiment is that it provides a means to follow or track bacteria to be released into a sample environment which already contains the same type of bacteria (or closely similar bacteria) or which may be subject to introduction of the same type of bacteria (or closely similar bacteria) from a separate source. The bacteria being tracked can be distinguished from the other bacteria (i.e., bacteria which are essentially the same) by virtue of the presence of the cell-specific receptor which has been introduced into the bacteria being tracked. There is thus provided the opportunity of assaying for the presence of released bacteria in the presence of otherwise identical (but for the receptor component) bacteria, without cross reactivity (background).

An exemplary approach for monitoring Pseudomonas uses the lamb gene of E. coli which is known to be a receptor for the coliphage λ. See, G. Vries et al. (1984) Proc. Natl. Acad. Sci. USA 81:6080–6084, and R. Ludwig, (1987) ibid. 84:3334–3338, both of which are incorporated herein by reference. Expression of lamB renders Pseudomonas species susceptible to attachment of λ phage and injection of phage DNA. A recombinant λ phage carrying a reporter gene, e.g., an ice nucleation gene, usually under the control of a strong promoter, is constructed in a broad host range plasmid. A lamB gene is inserted (e.g., by homologous recombination) into the chromosome of the bacteria to be assayed. The assay is then conducted in accordance with the teachings herein.

One specific use of this approach is to monitor Pseudomonas bacteria (e.g., P. syringae), including Pseudomonas soil bacteria and Pseudomonas epiphytic bacteria, which are released into a specific environment or setting, e.g., soil, a greenhouse or field setting. At least some of the bacteria to be released are first transformed to express the bacteriophage-specific receptor. Then by collecting bacteria from the environment at a later time, the presence of the bacteria in the environment can be determined. The approach provides a means to follow the presence, the migration and the survivability of the bacteria.

The following examples are offered by way of illustration and not by way of limitation.

EXPERIMENTAL

1. Assay for Male (F*) E. coli.

INA transducing particles were prepared as follows. The pUC118 plasmid-M13 bacteriophage system (Vieira and Messing (1987) Meths. Enz. 153:3–11) was modified by inserting ice nucelation gene inaY (isolated from Pseudomonas syringae strain PS31, which strain is described in Deininger et al. (1988) J. Bacteriol. 170:669–675), into plasmid pLVC76; this plasmid also carries an M13 bacteriophage pac site. Transducing particles were then produced using a packaging-defective M13 helper phage. The inaY gene was under the control of a lac promoter derived from the original pUC118 plasmid, and the resulting transducing particles retained the specificity of M13 phage for male (F+) strains of E. coli.

The transducing particles were passed through a 0.2 μm filter (to remove any INA* cells remaining in the preparation) and found to be free from ice nucleation activity down to $-12°$ C. Efficiency of transformation of E. coli MV1193 (F+) was measured independent of ice nucleation activity based on the activity of an ampicillin resistance gene carried by pLVC76. Plating assays of cells (100 μl: $OD_{600}=0.001$) exposed to the INA transducing particles (10 μl) were performed by incubation at 37° C. for 30 min., dilution to 1 ml, and plating of 50 μl aliquots. The results are set forth in Table 2.

TABLE 2

| Transfecting Particle Dilution | Colonies Recovered (− ampicillin) | Colonies Recovered (+ ampicillin) |
|---|---|---|
| $10^0$ | 404 | 45 |
| $10^{-1}$ | 792 | 45 |
| $10^{-2}$ | 865 | 6 |
| $10^{-3}$ | 838 | 1 |
| $10^{-4}$ | equivalent to $10^{-3}$ | 0 |

The transducing particles produced two effects. First, they reduced cell viability. Such reduced viability was probably caused by helper phage, the packaging-defective phage which were used to construct the particles, and which contaminate the transducing particles. Second, they transformed some cells to ampicillin resistance. Five of the ampicillin-resistant colonies were checked for ice nuclei; all colonies tested were INA+. If the number of colonies recovered at low phage concentrations, in the absence of ampicillin, is used to estimate the number of bacteria originally present, then the transformation efficiency at high phage concentrations was about 5%.

Samples of E. coli MV1193 were tested as follows. Cells (100 μl, $OD_{600}=0.01$) were incubated with 10 μl of a suspension of INA transducing particles ($10°$ dilution) at 37° C. for 2 hours, then at room temperature for 1 hour. The samples were then tested for ice nucleation activity in a standard droplet freezing assay consisting of 40×10 μl drops per dilution, with dilution by decades from $10^{-1}$ to $10^{-5}$ of the original sample concentration. The results of the freezing assay are set forth in Table 3.

TABLE 3

| T(°C.) | Nuclei per ml (no TP's)[1] | Nuclei per ml (no cells) | Nuclei per ml (cells + TP's) | % Nuclei per original cells[2] |
|---|---|---|---|---|
| −3.7 | 0.0 | 0.0 | $3.0 \times 10^1$ | 0.002% |
| −4.1 | 0.0 | 0.0 | $6.9 \times 10^2$ | 0.099% |
| −4.6 | 0.0 | 0.0 | $1.6 \times 10^3$ | 0.23% |
| −5.2 | 0.0 | 0.0 | $8.2 \times 10^3$ | 1.2% |
| −6.2 | 0.0 | 0.0 | $1.6 \times 10^4$ | 2.3% |
| −7.3 | 0.0 | 0.0 | $2.4 \times 10^4$ | 3.5% |
| −8.2 | 0.0 | 0.0 | $2.5 \times 10^4$ | 3.6% |
| −9.3 | 0.0 | 0.0 | $1.4 \times 10^5$ | 19.8% |
| −11.1 | 0.0 | 0.0 | $3.0 \times 10^5$ | 42.8% |

[1]TP's are transducing particles.
[2]The original concentration of cells was calculated using the approximate relationship that an $OD_{600}$ of 1.0 is $7.0 \times 10^8$ cell/ml. The detection limit was 5 nuclei/ml.

After 3 hours, the test measured the number of cells in a dilute suspension, with a sensitivity (approx. 40%) approaching that of a plating assay (approx. 90%). The plating assay requires about 15 hours for *E. coli*. The background was below the limit of detection. Therefore, the signal:noise ratio was at least $10^5$. The data showed the temperature-dependent sensitivity which is typical of ice nucleation assays, with the data point at $-11°$ C. being indicative of the total number of cells transformed to the INA+ phenotype.

In order to test for biological specificity of the INA transducing phage, an F- strain of *E. coli* (JE5505, a K12 derivative) was tested using the same protocol described above for *E. coli* MV1193. Attempted transduction of the *E. coli* JE5505 gave rise to no detectable nuclei. Antibiotic sensitivity or resistance was tested for as follows. The experiment was essentially the same as that described in connection with Table 3, except that the bacteria were first incubated with tetracycline (10 μg/ml), chloramphenicol (50 μg/ml) or no antibiotic (control) for 30 min at 37° C. The results of this experiment are set forth in Table 4.

TABLE 4[1]

| T(°C.) | Nuclei per ml (+ tetracycline) | Nuclei per ml (+ chloramphenicol) | Nuclei per ml (control) |
|---|---|---|---|
| −3.6 | $1.1 \times 10^1$ | 0.0 | 0.0 |
| −4.0 | $2.9 \times 10^2$ | 0.0 | $1.1 \times 10^2$ |
| −4.7 | $4.3 \times 10^3$ | 0.0 | $4.3 \times 10^3$ |
| −5.4 | $9.2 \times 10^3$ | 0.0 | $1.1 \times 10^4$ |
| −6.3 | $1.8 \times 10^4$ | 0.0 | $2.0 \times 10^4$ |
| −7.2 | $3.2 \times 10^4$ | 0.0 | $3.0 \times 10^4$ |
| −8.3 | $4.3 \times 10^4$ | 0.0 | $3.2 \times 10^4$ |
| −10.2 | $3.0 \times 10^5$ | 0.0 | $3.0 \times 10^5$ |

[1]Test conditions were as for Table 3, except that cells were preincubated for 30 min. at 37° C. with the antibiotic shown, before the addition of the INA transducing particles.

The assay correctly measured the number of tetracycline resistant bacteria in the sample, and correctly determined that all of these bacteria were chloramphenicol-sensitive. Thus, the assay of the present invention is suitable to screen for antibiotic resistance and sensitivity.

2. Assay for *Salmonella typhimurium*.

A low frequency transducing particle capable of conferring ice nucleation activity was obtained by homologous recombination of plasmid pRLG61 with bacteriophage P22. Plasmid pRLG61 contains the ice nucleation gene inaW (isolated from *Pseudomonas fluorescens* MS1650 as described in Corotto et al. (1986) EMBO J. 5:231–236) under the transcriptional control of the tac promoter (Bagdasarian et al. (1983) Gene 26:273–282). The origin of replication and an ampicillin resistance gene are derived from pBR322 (Bolivar et al. (1977) Gene 2:95–113), and pRLG61 contains a 4.3 kb insert of P22 DNA which was cloned from a HindIII digest of the P22 chromosome. pRLG61 was constructed in vitro and cloned in *E. coli*. Using a plasmid mobilization system, it was then transferred by conjugation into *Salmonella typhimurium* strain LT2. An ice nucleation assay for the pRLG61 (LT2) strain (designated RGS1) demonstrated a high level of ice nucleation activity.

INA transducing particles were prepared by infecting a liquid culture of RGS1 with wild-type P22 phage at a multiplicity of infection (m.o.i.) of 5 plaque forming units (PFU) per cell. The infected culture was incubated several hours and a raw phage-containing lysate prepared by treatment of the culture with chloroform (to lyse bacterial cells) followed by centrifugation (to pellet cell debris). The phages remained in the supernatant fraction along with various cellular material, including still-active ice nuclei. Subsequent centrifugation through a cesium chloride block gradient separated phage particles (which were collected from the 3M/5M interface) from the ice nuclei and other proteinaceous cellular contaminants (Davis et al. (1980) *Advanced Bacterial Genetics*, Cold Spring Harbor Laboratory, Cold Spring Harbor, N.Y., pp 80–82). Finally, the phage-containing fraction was dialyzed to remove the cesium chloride, then filtered through a 0.45 μm filter to sterilize the preparation.

Due to the nature of their formation, the proportion of transducing particles to wild-type phages in such a preparation was small. The detection of ice nucleation activity and the recovery of drug-resistant transductants from a transfected culture (see below) both indicated that the transducing particle preparation was able to generate a single transduction event for approximately each 1000 normal lytic infections.

A preparation of low-frequency transducing particles (derived by infection of RGS1 with P22 as described above) was used to transduce the inaW gene into a culture of *S. typhimurium* LT2. Relatively high-density cultures were used to help protect transduced cells from lethal super-infection by the wild-type phages which are the majority species in the transducing particle preparation. Additionally, ampicillin (Ap) was added to the medium following phage adsorption to the host cells, to further reduce the rate of lytic infections with wild-type P22 (neither the host cells nor the wild-type phages were resistant to Ap). The species-specificity of the transducing phages was tested by parallel transfection of *E. coli* strain AB1157 with the transducing particle preparation.

Late log-phase cultures ($OD_{600}=0.5-1.0$) of *S. typhimurium* LT2 and *E. coli* AB1157 were infected with the transducing particle preparation at an m.o.i. of approximately 0.1 PFU per cell. Cultures were incubated at 37° C. without agitation and particles were allowed to adsorb to host cells for a period of 20 min. Control samples were run in parallel and consisted of sterile broth "infected" with transducing phages and uninfected bacterial cultures. Ap was added to the infected cultures, and incubation continued for an additional 40 min. at 37° C. with agitation. Cultures were then incubated at 24° C. for 1 hour to allow expression of ice nucleation activity.

Ice nucleation assays were then performed as described above for *E. coli* in connection with Table 3. $OD_{600}$ of the LT2 and AB1157 cultures was measured at 1.0 and 0.67, respectively. The results are set forth in Table 5 below.

TABLE 5

| T(°C.) | TP's no cells | LT2 uninfected | AB1157 cells + TP's | LT2 cells + TP's | % INA+ LT2 cells + TP's |
|---|---|---|---|---|---|
| −5.7 | 0 | 0 | 0 | $8.7 \times 10^1$ | $1.2 \times 10^{-5}$ |
| −6.0 | 0 | 0 | 0 | $2.9 \times 10^2$ | $4.1 \times 10^{-5}$ |
| −7.0 | 0 | 0 | 0 | $1.8 \times 10^3$ | $2.6 \times 10^{-4}$ |
| −8.0 | 0 | 0 | 0 | $8.7 \times 10^3$ | $1.2 \times 10^{-3}$ |
| −9.0 | 0 | 0 | 0 | $3.9 \times 10^4$ | $5.6 \times 10^{-3}$ |
| −10.0 | 0 | 0 | 0 | $2.1 \times 10^5$ | $3.0 \times 10^{-2}$ |
| −11.0 | 0 | 0 | 0 | $2.7 \times 10^5$ | $3.9 \times 10^{-2}$ |
| −12.0 | 0 | 0 | 0 | $2.7 \times 10^5$ | $3.9 \times 10^{-2}$ |

The table presents the ice nucleation activity of experimental samples as a function of temperature. The cumulative frequency of ice nuclei per ml of original culture is give for particular temperature points. The last column (% INA+ LT2) represents the number of ice nuclei per ml expressed as a percent fraction of the cell population, estimated to be $7 \times 10^8$ cells/ml for $OD_{600} = 1.0$.

The above results demonstrate that the expression of ice nucleation activity occured only as a result of the infection of a susceptible host strain (LT2) with the transducing phage preparation. Neither the host cells nor the phages by themselves expressed any detectable ice nucleation activity. Furthermore, this experiment has confirmed the host strain specificity of the particles may be maintained after transduction of the inaW gene, since no detectable transduction of ice nucleation activity was observed in *E. coli* AB1157. As an indication of the transduction frequency, the maximum frequency of ice nuclei observed in the above experiment, $2.7 \times 10^5$ per ml, corresponded to $1 \times 10^{-3}$ ice nuclei per PFU of the transducing phage preparation.

Transduction of plasmid pRLG61 was also detected by recovery of ampicillin-resistant colonies from the transfected culture. After infection and initial incubation as described above, the cells were spread on agar medium containing ampicillin. The agar surface was previously coated with a layer of heat-killed LT2 to adsorb and thus protect recipient cells from the lethal wild-type phages in the preparation. Ampicillin-resistant transductant colonies appeared after overnight incubation. The results indicated a transduction frequency for pRLG61 of $6 \times 10^{-3}$ Ap$^r$ colonies per PFU of the transducing phage preparation. Thus, two separate experiments have determined the frequency of transduction of this system to be in the range of $10^{-3}$ to $10^{-2}$ transduction events per PFU of the transducing particle preparation.

In summary, low-frequency transducing particles were prepared by transduction of ice nucleation gene into phage P22. Particles so produced were then transduced into *Salmonella typhimurium* strain LT2 and found to confer readily detectable ice nucleation activity. Background ice nucleation activity in experimental control samples was found to be absent, and no ice nucleation activity resulted upon the attempted transfection of a bacterium, *E. coli*, which is non-permissive for P22.

3. Phage P22 High Frequency Transduction System

The following describes a high frequency transduction (HFT) system which was developed using phage P22. This system allowed the high-frequency transduction of the inaW gene to susceptible strains of Salmonella.

The HFT system was constructed so that the transduced reporter gene (the inaW ice nucleation gene from *Pseudomonas fluorescens*) existed as a permanent cointegrate with a P22 prophage, contained in a lysogenic strain of Salmonella which was used to produce the high-frequency transducing particles/phages (HFTPs). Propagation of the HFTP-producing strain resulted in a culture in which every cell was a potential producer (upon induction of the recombinant prophage's lytic cycle) of TPs, yielding a high proportion of TPs to non-transducing, wild-type revertant phages.

Two basic components were used to construct the HFT system: i) a polA mutant strain of *S. typhimurium* (defective for DNA polymerase I), and ii) plasmid pRLG68, a mobilizable plasmid encoding ice nucleation activity and ampicillin (Ap) resistance, with a ColE1-type origin of replication.

The polA strain, called AA3007 (Whitfield and Levine, (1973) J. Bacteriol. 116:54–58), was used specifically because it is unable to support the autonomous replication of ColE1-derived plasmids. To facilitate its use in subsequent manipulations, a spectinomycin-resistant (Sc$^r$) derivative of AA3007 was first selected as follows: A culture of AA3007 was grown in 5 ml L-broth (LB) overnight (ON) at 37° C.; 2 ml of the ON culture was used in turn as inoculum for a 200 ml L-broth culture which contained Sc at a concentration of 100 μg/ml. After growth for 24 h., replicate platings of the culture were made on LB+Sc (Sc at 50 ug/ml) plates, using 50 ul of the 24 h. liquid culture per plate. Sc$^r$ colonies were identified and isolated after 24 h. growth of the plates at 37° C. One such Sc$^r$ colony was the origin of the AA3007 Sc$^r$ strain, hereafter designated RGS10. Growth of P22 on RGS10 was confirmed, and a derivative which had become lysogenic for P22, called RGS11, was isolated by streaking cells from the turbid center of a P22 plaque formed on a lawn of RGS10.

Another key element of the HFT system was plasmid pRLG68, which was designed to facilitate the incorporation (via homologous recombination) of a highly-expressed inaW (ice nucleation) gene into the P22 prophage of strain RGS11. pRLG68 was constructed in two steps. First, a clone of inaW, obtained on a 4.6 kb BamHI/HindIII restriction enzyme fragment, was cloned into the expression vector plasmid pKK223-3 (Brosius and Holly (1984) Proc. Natl. Acad. Sci. USA 81:6929–6983). pKK223-3 contains the ampicillin-resistance (Ap$^r$) gene, origin of replication, and "bom" site (which allows it to be mobilized by certain bacterial conjugation systems) of pBR322 (Bolivar et al. (1977) Gene 2:95–113); in addition, it contains the powerful tac promoter (de Boer et al. (1983) Proc. Natl. Acad. Sci. USA 80:21–25) situated so as to provide promotion to foreign genes inserted proximally in the plasmid's polylinker (multi-cloning-site) region. The intermediate inaW/pKK223-3 construct was called pRLG66. The second and final stage of the construction of pRLG68 involved the insertion of a fragment of P22 chromosomal DNA into a site in pRLG66. The 2.5 kb P22 fragment known as BamHI fragment "B" in the P22 physical map (Rutila and Jackson (1981) Virology 113:769–775) was purified from a BamHI digest of the P22 chromosome, and inserted in the unique BamHI site (just upstream of the tac promoter region) of pRLG66 so as not to interrupt any essential plasmid functuations, nor interfere with the expression of inaW. The P22 fragment was chosen for its lack of genes essential to the basic life cycle of P22, since it would ultimately be the point of insertion of foreign DNA in the P22 prophage during the construction of the HFTP-producing strain. The resulting P22/pRLG66 construct was called pRLG68.

The bom region of pRLG68 (derived ultimately from its pBR322 predecessor) allowed it to be mobilized and transferred during bacterial conjugation, so long as conjugation and mobilization functions were provided in trans by the conjugal donor strain. Thus, pRLG68 was transformed into the *E. coli* strain GJ23, in which it was mobilizable by the R64drd11/pGJ28 system (Van Haute et al. (1983) EMBO J. 2:411–417), and from there transferred via inter-species conjugation to RGS11. Since pRLG68 could not autonomously replicate in the recipient RGS11 strain (due to the polA mutation), any Ap$^r$Sc$^r$ progeny from the mating were assumed to contain pRLG68 insertions in the P22 prophage, resulting from homologous recombination between the plasmid's region of P22 DNA and the homologous region in the prophage. A Southern blot analysis of a few representative clones (alongside their AA3007 and RGS11 progenitor strains) gave results consistent with the formation of such a pRLG68/P22 cointegrate. The resulting strain was called RGS12, and was the strain from which HFTPs were produced.

HFTPs were produced from RGS12 by treatment of cultures of the strain with Mitomycin-C, a drug which is known to induce the lytic cycle in lysogens of P22 and other such phages (Arber et al. (1983) in Lambda II, Cold Spring Harbor Laboratory, Cold Spring Harbor, N.Y. pp 443–445). Such induction of RGS12 resulted in the replication and packaging of progeny phage particles, many of which were recombinant HFTPs. A culture of RGS12 was grown in L-broth at 37° C. to mid-exponential phase ($A^{600}$ =0.40), at which point Mitomycin-C was added to a final concentration of 5 mM. The culture flask was covered with foil to block any light that would stimulate the bacterial photo-active DNA repair mechanism (thus possibly compromising the efficiency of induction), and incubation resumed for several hours until the bacterial cells had lysed completely. Bacterial debris was cleared from the lysed culture by centrifugation at 2,000×g for 20 min., and the supernatant was sterilized by passage through a 0.45 um filter. Additionally, the RGS12 supernatant was heated 15 min. at 55° C., as this was found to destroy residual ice nucleation activity (as assayed by a standard droplet-freezing assay of the material) without adversely affecting the HFTPs themselves. As an experimental control, phages were produced from RGS11 (the non-recombinant, lysogenic progenitor strain of RGS12) in an identical manner.

Some experiments were done to characterize the RGS12 HFTPs. First, the titers of phage preparations from the mitomycin-C-induced RGS11 and RGS12 cultures were compared with a sample of phages produced from a similarly treated, non-mutant LT2(P22)+ lysogenic strain (LT2 is a vigorous, non-mutant ancestor strain of RGS11 and RGS12). The titers were approximately $10^9$, $10^8$ and $10^7$ PFU/ml for the LT2(P22)+, RGS11 and RGS12 preparations, respectively. Since phage titers are measured by counting plaques formed on a bacterial lawn, only phages able to undergo lytic infection are assayable. The relatively low titer of the RGS12 preparation indicated a significant proportion of TPs, since most TPs will be defective for lytic growth (the heterologous DNA which they contain would crowd out essential genes). This was confirmed by the electrophoretic analysis of restriction digests of purified RGS11 and RGS12 phage DNAs, which showed the presence of extra restriction fragments in the RGS12 phage DNA. The sizes of the extra fragments corresponded with those predicted for the pRLG68/P22 prophage cointegrate; moreover, their relative intensities showed that most of the phage particles contained the extra DNA.

The following work used the same preparation of RGS12 HFTPs, prepared as described above. The detection of bacterial cells by the transduction of ice nucleation activity (INA) using RGS12 HFTPs will hereafter be referred to as a "transduction assay". The transduction assay procedure involved the infection, with HFTPs, of samples which contain bacteria, and the eventual determination of ice nucleation activity (INA) expressed in the samples. Initial experiments were done to characterize and optimize the detection of bacteria using the HFTP system. Eventually, experiments were done to simulate the assay of bacteria in real food samples, such as the example described below.

The following experiment was done to demonstrate the detection of Salmonella present in a whole egg mixture. A culture of *S. typhimurium* strain LT2 was grown in L-broth at 37° C. to an optical density ($A_{600}$) of 0.35. The culture was then diluted in a series of 10-fold increments into raw, blended egg (i.e., the yolk and white were homogenized together); the dilution series in egg extended to $10^{-5}$ relative to the original ($A^{600}$=0.35) culture. Bacteria were assayed by transduction using RGS12 HFTPs as follows: 40 ul samples of each of the $10^{-2}$ to $10^{-5}$ bacterial dilutions in egg were added to 360 ul of sterile L-broth, which constituted a 10-fold dilution of the original samples. Additionally, control samples of the un-inoculated egg mixture were prepared in a similar manner (diluted 1:10 in LB). To each sample was added 100 ul of RGS12 HFTP preparation (which contained $2\times10^6$ pfu total), except for one of the un-inoculated egg controls, which instead received an equivalent amount of sterile L-broth. The samples were then incubated for 1 h. at 37° C. followed by 1 h. at 23° C., to allow expression of transduced INA. The INA of transduced samples was then measured by a droplet freezing assay as follows. To each transduced sample was added 1/100 volume of a fluorescent dye mixture (100 mM carboxy-fluorescein, 100 mM tris-HCl pH 7.0) which aided in the detection of freezing events during the assay (the dye color changes from fluorescent yellow to dull red upon freezing). Dilutions of each sample were then made in decades from $10^{-1}$ to $10^{-5}$) into the same carboxyfluorescein buffer (at 1 mM strength in all dilutions). $20\times10$ μl droplets of each dilution ($10^0$ to $10^{-5}$) of the original assay samples (which were themselves transduced dilutions of the original bacterial culture) were then placed on paraffin-coated foil which floated on the surface of a temperature-controlled chilling bath. The freezing of droplets was then monitored as the temperature of the bath was lowered from $-2.0°$ C. to $-12.0°$ C. over a period of 80 minutes. The raw frozen droplet data was then used to calculate the frequency of ice nuclei in the original samples (Vali (1971) J. Atmos. Sci. 28:402–409). In its final form, the data are expressed as a temperature spectrum of cumulative INA, i.e., as numbers of ice nuclei per ml at a range of temperature points. The results for the above experiment are presented in Table 5.

TABLE 5[1]

| Sample | Bacteria/ml | $-6°$ C. INA | $-12°$ C. INA |
| --- | --- | --- | --- |
| 1. Un-inoculated Egg (no HFTPs) | 0 | 0 | 0 |
| 2. Un-inoculated Egg + HFTPs | 0 | 0 | 0 |
| 3. $10^{-2}$ Culture/Egg + HFTPs | $2.5 \times 10^5$ | $3.0 \times 10^4$ | $6.9 \times 10^5$ |
| 4. $10^{-3}$ Culture/Egg + HFTPs | $2.5 \times 10^4$ | $1.3 \times 10^3$ | $4.7 \times 10^4$ |
| 5. $10^{-4}$ Culture/Egg HFTPs | $2.5 \times 10^3$ | $1.6 \times 10^2$ | $4.5 \times 10^3$ |
| 6. $10^{-5}$ Culture/Egg + | $2.5 \times 10^2$ | $5.1 \times 10^0$ | $1.6 \times 10^1$ |

TABLE 5¹-continued

| Sample | Bacteria/ml | −6° C. INA | −12° C. INA |
|---|---|---|---|
| HFTPs | | | |

¹The above data shows the results of INA assays performed on transduced samples. Bacteria/ml was estimated from the $A_{600}$ of the original culture (according to the equivalency $A_{600} = 0.7 = 5 \times 10^8$ cells/ml), taking into account the 1:10 dilution of the bacteria/egg mixtures into LB to prepare the samples for transduction.

As shown in Table 5, the transduction of INA using the HFT system allowed the detection of LT2 cells in all samples in which they were present, even at as low a concentration as 250 cells/ml (after dilution in LB prior to the addition of HFTPs). Also apparent from the un-inoculated egg samples is the absence of background activity where no bacteria were present. The INA observed in such experiments had a strong event-counting nature, in that individual INA+ cells were detected. One simplication of this is that, since a majority of cells in a sample were transduced to the INA+ phenotype, the frequency of INA of the sample allowed the estimation of the bacterial cell density. Thus, the measurement of INA at −12° C. (at which temperature the detection of INA is the most sensitive) was strongly correlated with the population of LT2 cells in the sample.

In summary, a high frequency transduction system was developed in phage P22, in which the transduction of a tac-promoted inaW gene was maximized by manufacturing transducing particles from a Salmonella strain containing an ice nucleation gene in a P22 prophage. After verification of its structure by DNA analysis techniques, the HFT system was used in a transduction assay to detect LT2 cells present in samples of inoculated raw egg. The transduction assay showed very high sensitivity in detecting sparse populations of bacteria, with no background signal, and demonstrated that the assay could be used to estimate the number of bacterial cells present.

4. Transduction in Heat-Disabled Cells

This example describes a set of experiments designed to test the response of disabled bacteria to phage transduction, and to determine how much recovery time may be necessary before such bacteria become detectable by the method.

Cell damage was induced in cultures of *Salmonella typhimurium* LT2 by exposure to injurious high temperature, during which time aliquots were removed at successive time points and plated on L agar (a rich, nonselective medium) and SS agar (a stringently selective medium used in the isolation of Salmonella and Shigella). After overnight incubation, the relative numbers of colonies which grew on L and SS agars for each heat-treated aliquot were used to gauge the extent of damage caused by the heat treatment. The experiment below describes the results of transduction of heat damaged cells using the high frequency transduction (HFT) system described in previous example (Example 3).

In the following experiment, a dilute culture of LT2 was exposed to 55° C. by immersion in a water bath. Sample aliquots were removed from the culture at time 0 (i.e., just before immersion in the water bath), and at times 60, 90, 120 and 150 seconds following immersion. Dilutions of the aliquots were plated on L and SS agars immediately, to allow the assessment of the initial damage done to the bacteria. Each aliquot was then divided to make two identical sets of heat-treated aliquots. One set was transduced using RGS12 transducing phages using a method (as described in Example 3) which involved a total of 2 hours of incubation: 1 hour at 37° C. followed by 1 hour at 23° C. The other set of aliquots was not transduced, but was incubated in parallel with the transductions as a control for the recovery of the heat disabled cells during the transduction procedure (this observation would have been obscured in the phage-infected aloquots). Dilutions of the untransduced control aliquots were then plated on L and SS agars at the end of the transduction incubations, while assays were done to measure the INA expressed by the transduced sample aliquots. The results of the experiment are presented in Table 6.

TABLE 6

| | Seconds at 55° C. | | | | |
|---|---|---|---|---|---|
| | 0 | 60 | 90 | 120 | 150 |
| Initial cfu/ml (LB) | $1.4 \times 10^5$ | $1.1 \times 10^5$ | $9.1 \times 10^4$ | $3.5 \times 10^4$ | $7.0 \times 10^3$ |
| Initial cfu/ml (SS) | $1.4 \times 10^5$ | $9.7 \times 10^4$ | $8.0 \times 10^3$ | <DL | <DL |
| Final cfu/ml (LB) | $1.2 \times 10^6$ | $4.4 \times 10^5$ | $1.0 \times 10^5$ | $1.7 \times 10^4$ | $4.0 \times 10^3$ |
| Final cfu/ml (SS) | $1.4 \times 10^6$ | $4.3 \times 10^5$ | $7.0 \times 10^4$ | $5.0 \times 10^3$ | <DL |
| Initial % Disabled | 0 | 12 | 91 | >97 | >97 |
| Final % Disabled | 0 | 2 | 30 | 71 | >25 |
| −12° C. Ice Nuclei/ml | $8.0 \times 10^4$ | $7.4 \times 10^4$ | $5.0 \times 10^4$ | $1.3 \times 10^4$ | $5.1 \times 10^2$ |

¹Comparison of plate counts and INA of sample aliquots taken from heat-disabling experiment. Colony counts on individual plates have been translated into colony forming units (cfu) per ml as for the undiluted culture, so as to be directly comparable with INA data. "<DL" indicates where colony counts fell below the detection limit (i.e., no colonies were detected at the dilutions plated); DL for the platings of this experiment was $1 \times 10^3$ cfu/ml. "% Disabled" values were figured as 100-% (cfu on SS/cfu on L); when no colonies had been observed on SS plates, the highest value below the detection limit for the platings was substituted in the calculation.

One obvious effect of the heat treatment was the outright killing of cells, which reduced the viable cell population by 95% by the end of the time course. Also apparent was the increasing proportion of disabled cells among survivors collected at later time points; i.e., progressively fewer of the LB-platable cells were able to grow on SS agar. As can be seen in Table 6, aliquots removed after 90 sec. contained mostly or entirely disabled cells. Especially in these latter samples, the effects of the heat treatment persisted to the end of the transduction procedure; the cultures failed to divide and apparently, in the 120 sec. and 150 sec. aliquots, may have suffered additional mortality during the following 2 hours. However, despite the absence of growth in the severely damaged aliquots, there was some degree of recovery from the disabled state during the time taken to perform the transduction assays. The degree of recovery was less in the more severely damaged samples, in which a majority of cells initially disabled remained in that state to the end of the procedure.

The results presented in Table 6 indicate that the frequency of ice nuclei expressed in the transduced samples corresponded closely to the respective populations of viable bacteria (i.e., cells which survived heat treatment in either a disabled or non-disabled state); this was true even when the initial population consisted entirely of disabled cells. An important corollary to this is that cells which had been killed by the heat treatment were invisible to the assay. In short, the response of heat-disabled bacteria to detection by transduction was virtually the same as that of healty cells. These results show that the phage transduction assay may be performed without the need for a recovery period to ensure the detection of disabled cells.

To summarize, cell damage was induced in cultures of S. typhimurium strain LT2 by exposure to 55° C. for varying lengths of time. Platings of the heat-damaged samples or LB agar and SS agar were then done; the difference in the numbers of bacterial colonies which grew on the two media was used as a measure of damage to the bacterial culture. Transduction assays were then performed on such heat-disabled bacteria using the RGS12 HFTP system. The results of the assays indicated that disabled bacteria were detected with equal efficiency to healthy bacteria, and that bacteria which had been killed by the treatment became invisible to detection by the assay.

5. The Host Range Specificity of a P22 Transducing Phage

The following experiments were done to test the response of a P22-derived transduction system in assaying a number of different Salmonella serotypes from various serogroups. The "high-frequency transduction" (HFT) system described in Example 3 was used in the following experiments. High-frequency transducing particles/phages (HFTPs) carry a highly-expressing gene (tac-promoted inaW) encoding ice nucleation activity (INA), and were shown in Example 3 to allow the sensitive detection of S. typhimurium strain LT2 cells. The following set of experiments demonstrated that P22-derived TPs obeyed the known host range of P22 (since the biological specificity of the transduction assay is one of its key features), that different susceptible bacterial strains were transducible/detectable with equal efficiency, and that the presence of non-P22-susceptible bacteria in the assay samples did not interfere with the detection of susceptible bacteria. The results from two experiments are presented below: one examined transduction in pure cultures of bacteria, while the other examined transduction in mixed cultures.

A. Pure Cultures

Several Salmonella strains which included 9 different serotypes belonging to serogroups B, D, $C_1$, $C_2$ and $G_2$ of the Kauffmann-White classification scheme for the genus Salmonella (Kauffmann (1978) *Das Fundament*, Munksgaard, Copenhagen), were provided by Dr. B. Stocker. The known presence or absence of the P22 receptor molecule in the outer membranes of the various strains allowed them to be grouped as P22-sensitive (P22$^s$) or P22-resistant (P22$^r$); thus, strains belonging to serogroups B and D are P22$^s$ while those belonging to serogroups $C_1$, $C_2$, and $G_2$ are P22$^r$. Transduction assays were performed on pure cultures of each bacterium to confirm that transduction would only occur in known P22$^s$ strains. S. typhimurium strain LT2 (P22$^s$) was included in the panel as a control, since its behavior in transduction by the HFT system had been previously determined (see Example 3).

Pure cultures of each strain were grown in L-broth at 37° C. to mid-exponential phase ($A_{600}$ ranged from 0.28 to 0.67); serial dilutions of each culture were then made (using sterile LB as the diluent) in decades down to $10^{-7}$ relative to the original culture. Transduction using RGS12 (prepared as in Example 3) HFTPs was then performed according to the method outlined in Example 3. Small aliquots of each culture dilution (0.1 ml) were prepared, each of which received 25 ul of HFTP preparation containing $3 \times 10^6$ pfu total. The samples were incubated 1 hour at 37° C. followed by 1 hour at 23° C. After incubation, a small amount (1 ul) of a concentrated fluorescent dye (used to aid in the detection of freezing events during the subsequent INA assay) was added to each transduced culture dilution as described in Example 3. Three replicate 10 ul droplets of each transduced dilution were then placed in separate wells of a 96-well microtiter dish. The microtiter dish was then placed on a form-fitted chilling block which was equilibrated at −10.0° C. After 10–15 minutes, the number of frozen drops was tallied. Results are shown in Table 7.

TABLE 7

| Strain | Sample/Dilution | | | | | | |
|---|---|---|---|---|---|---|---|
| | 10−1 | 10−2 | 10−3 | 10−4 | 10−5 | 10−6 | 10−7 |
| S. gallinarium ($D_1$) | 3 | 3 | 3 | 3 | 3 | 3 | 3 |
| S. dublin ($D_1$) | 3 | 3 | 3 | 3 | 3 | 3 | 3 |
| S. bovis-morbificans ($C_2$)* | 0 | 0 | 0 | 0 | 0 | 0 | 0 |
| S. havana ($G_2$)* | 0 | 0 | 0 | 0 | 0 | 0 | 0 |
| S. enteritidis ($D_1$) | 3 | 3 | 3 | 3 | 3 | 3 | 3 |
| S. paratyphi-B (B) | 3 | 3 | 3 | 3 | 3 | 3 | 3 |
| S. typhimurium (B) | 3 | 3 | 3 | 3 | 3 | 3 | 3 |
| S. cholerae-suis (C1)* | 0 | 0 | 0 | 0 | 0 | 0 | 0 |
| S. typhi ($D_1$) | 3 | 3 | 3 | 3 | 3 | 3 | 2 |
| LT2 (B) | 3 | 3 | 3 | 3 | 3 | 3 | 3 |

[1]Each of the $10^{-1}$ to $10^{-7}$ dilutions of Salmonella strains was assayed for INA following transduction with HFTPs. INA was measured at a constant temperature of −10.0° C. The data presented are numbers of drops of each sample dilution which froze, out of a total of 3 replicate drops per sample dilution. The serogroup of each strain is shown in parentheses next to the strain name; asterisks denote strains which are P22$^r$, the remainder are P22$^s$.

The results presented in Table 7 show that the transduction of INA occurred only among the P22$^s$ strains, and that furthermore, the susceptible bacteria were detected with equally high sensitivity in every case. Among the P22$^r$ strains, no background of INA was detected. Based on the $A_{600}$ measurements of the original (undiluted) log-phase cultures, the cell populations of the corresponding $10^{-7}$ dilutions (and hence the minimum detection limit in this experiment) were fewer than 100 cells/ml. This level of sensitivity agreed with that observed previously with strain LT2 alone (see Example 3). This experiment thus demonstrated that P22-mediated transduction obeyed the known host range of the phage, and that a variety of P22$^s$ strains could be transduced with equal, and high, efficiency.

B. Mixed Cultures

Another aspect of the specificity of the transduction assay is the effect that "non-target" bacteria (i.e. miscellaneous bacteria not expected to be detected by the transduction assay) might have on the detection of P22$^s$ bacteria by phage transduction. The following experiment was done to examine transduction in such a setting.

RGS12 HFTPs were used in this experiment similarly to the method of part A of this Example except as stated otherwise below. Only one P22$^s$ strain, S. dublin, was used and the samples were prepared so that S. dublin was assayed while in the presence of a P22$^r$ bacterium. The P22$^r$ bacteria were: E. coli strain JC10291 (Willis et al. (1981) Mol. Gen. Genet. 183 479–504), B. subtilis strain BR151 (ATCC No. 33677), and S. havana (a naturally P22$^r$ strain of Salmonella)—see part A of this Example. Each strain was grown in L broth at 37° C. to mid-exponential phase, at which time $A_{600}$ readings were made. The cultures were then adjusted (by dilution in fresh L broth) to the same density ($A_{600}=0.36$).

Control transductions of individual strains were done to check the background (if any) in the P22$^r$ bacteria, and to measure the response of the assay with a pure culture of S. dublin. The S. dublin samples were prepared by diluting the original ($A_{600}=0.36$) culture in decades down to $10^{-9}$; only the $10^{-2}$ to $10^{-9}$ dilutions were used in the assay. Four such dilution series were prepared: in one, sterile LB was used as the diluent; in the other three, one of each of the undiluted ($A_{600}-0.36$) cultures of P22$^r$ bacteria was used as the diluent. In other words, each such sample series consisted of eight dilutions in which the concentration of S. dublin ranged from $10^{-2}$ to $10^{-9}$ (relative to the original culture). Since one of the other undiluted cultures was used as the diluent for the S. dublin dilution series, the other bacterium was present at undiluted strength in each of the S. dublin dilutions. So, each P22$^r$ bacterium was present in a range of excess: from $10^2$-fold (in the $10^{-2}$ S. dublin dilutions) to $10^9$-fold (in the $10^{-9}$ S. dublin dilutions).

Each sample/dilution contained 0.1 ml total volume, and each was transduced individually by adding 25 ul of RGS12 TPs (containing $3 \times 10^6$ pfu total). To accommodate the large number of individual samples, the procedure was performed in a sterile 96-well microtiter dish with lid. Incubations were done for 1 h. at 37° C. followed by 1 h. at 23° C. After incubations, a small amount (1 ul) of a fluorescent dye concentrate was added to each sample to aid in the detection of freezing events during the subsequent INA assays as described in Example 3. Four replicate 10 ul drops of each sample were then placed in separate wells of a flexible plastic 96-well microtiter dish which was placed on a form-fitted chilling block equilibrated at $-10.0°$ C. After 10–15 minutes, frozen drops were tallied. The results are shown in Table 8.

TABLE 8

| Sample Series | S. dublin Dilution Factor | | | | | | |
|---|---|---|---|---|---|---|---|
| | $10^{-3}$ | $10^{-4}$ | $10^{-5}$ | $10^{-5}$ | $10^{-7}$ | $10^{-8}$ | $10^{-9}$ |
| S. dublin (alone) | 4 | 4 | 4 | 4 | 4 | 1 | 0 |
| S. dublin + E. coli | 4 | 4 | 4 | 4 | 3 | 1 | 0 |
| S. dublin + B. subtilis | 4 | 4 | 4 | 4 | 1 | 2 | 2 |
| S. dublin + S. havana | 4 | 4 | 4 | 4 | 3 | 4 | 0 |

[1] Each dilution of each sample was assayed for INA following transduction with HFTPs. INA was measured at a constant temperature of $-10.0°$ C. Numbers in table indicate the number of droplets which froze for each dilution of sample series (out of a total of 4 drops per sample dilution). Numbers in column headings indicate the dilution factor of the S. dublin culture into undiluted cultures of the other bacteria (except where S. dublin was assayed alone).

The results shown in Table 8 demonstrate that the presence of other, P22$^r$, bacteria in the assay samples had no apparent effect on the detection of the target strain. The assay detected no background activity, either in the untransduced bacteria, or in the "transduced" (i.e. exposed to TPs) P22$^r$ bacteria. In other words, the P22$^r$ bacteria were invisible to the assay, and when present with a P22$^s$ bacterium, they exerted no significant effect on the detection of the bacterium. Because the results described above in Part A of this Example (using pure cultures) failed to reach the lower detection limit of the assay (i.e., the highest dilutions still froze), the dilution series was extended in the present experiment to $10^{-9}$ in an attempt to reach below the detection limit. Since the original cultures contained in the neighborhood of $10^8$ to $10^9$ cells (according to an estimate of bacterial population based on $A_{600}$), few if any cells would be expected in the $10^{-9}$ dilutions. Thus, these results show that, even in the presence of large numbers of non-target bacteria, the limit of detection of this assay extended close to the theoretical limit of any bacterial assay: the point at which no cells are present.

To summarize the above results, the response of a P22/inaW transduction system was tested against several bacteria which represented both P22-sensitive and P22-resistant strains. The response of the assay was assessed in terms of its predicted specificity (according to the known presence/absence of P22 receptors in individual strains), its sensitivity in the detection of susceptible strains, and its resistance to interference due to the presence of large numbers of non-susceptible bacteria. The assay proved to be strictly specific: no activity resulted in known P22$^r$ strains. Moreover, the sensitivity of the assay was equally high in all P22$^s$ strains which were assayed; in every case the assay performed at its optimal level as determined in previous experiments using strain LT2 alone. Finally, the sensitivity of the assay was shown to be unaffected by the presence of large numbers of P22$^r$ bacteria; the assay still performed at its optimal level.

6. Transduction of an Enzymatic Marker Gene

This example describes a bacterial assay based on the transduction of an enzymatic marker gene. The system used the P22-mediated transduction of a gene encoding beta-glucuronidase, or "GUS", activity; transduced, GUS+ bacteria were then detected by a fluorescent assay.

GUS activity is encoded by the uidA gene which was originally isolated from E. coli K12 (Jefferson et al. (1986) Proc. Natl. Acad. Sci. USA 83 8447–8451). It is a well-characterized enzymatic marker system which has been shown to function in a range of organisms from bacteria to higher plants (Jefferson et al. (1987) EMBO J. 6 3901–3907). Reagents for the fluorescent assay of GUS activity are commercially available.

The GUS transduction system was designed using phage P22, in a manner analogous to that used to construct the inaW high-frequency transduction system described in Example 3. In the present example, the uidA gene was incorporated into a P22 prophage, located in the chromosome of a lysogenic host bacterium, in such a way that induction of the phage's lytic cycle resulted in the replication and packaging of the uidA sequences along with the phage's own DNA.

The uidA clone was obtained from the plasmid PJJ3431, in which the gene had been modified slightly to provide an NcoI site at the start codon. The modifications introduced 5 extra amino acids to the amino terminus of the gene product; however, GUS activity was retained. The uidA gene was isolated on a 2.9 kb NcoI/PstI restriction enzyme fragment of pJJ3431 and cloned into the corresponding sites of the expression vector pKK233-2 (Brosius, et al. (1985) J. Biol. Chem. 266 3539-3541). pKK233-2 provided the uidA gene with a powerful hybrid promoter, called "trc", a ribosome binding site and a start codon; additionally, it encoded ampicillin resistance (Ap$^r$) and contained a region ("bom") which allowed it to be mobilized by certain bacterial conjugated systems. The resulting construct was called pRLG73.

pRLG73 was then furnished with a region of P22 DNA, to provide a target for homologous recombination which would allow the plasmid to be incorporated into a P22 prophage during a subsequent stage of the construction. The 2.5 kb P22 BamHI fragment "B" (as designated in the P22 physical map of Rutila and Jackson—see Example 3) was cloned into the unique BamHI site of pRLG73, just upstream of the trc promoter region. Since the P22 fragment would ultimately be the point at which the plasmid was inserted into the phage genome, it was selected so as not to interrupt any essential P22 genes. The resulting P22/pRLG73 plasmid was called pRLG80.

The following stages of the construction were performed exactly as the equivalent steps outlined in more detail for the inaW transduction system described in Example 3, with pRLG80 taking the place of pRLG68. pRLG80 was transferred by bacterial conjugation from an *E. coli* donor strain into an *S. typhimurium* recipient which was lysogenic for P22. Additionally, the *S. typhimurium* recipient, called RGS11, contained a mutation in one of its DNA polymerase genes (the mutant allele is designated "polA") which prohibited the autonomous replication of the pRLG80 plasmid. Hence, the only means of survival for pRLG80 in RGS11 was via integration into the P22 chromosome, which occurred within the region of homology carried on the plasmid. Such progeny cells were selected following the conjugation by means of the Ap$^r$ marker carried by pRLG80; the pRLG80-carrying progeny were also identified by the GUS activity which they expressed (visible when a colorimetric substrate for GUS was included in the plating medium).

The new P22/pRLG80 lysogenic strain was called RGS34, and was the strain which was used to produce uidA transducing phages (TPs). Production of TPs was accomplished by treating a liquid culture of RGS34 with the drug mitomycin-C, as described in Example 3. Mitomycin-C treatment results in the replication and packaging of progeny phage particles which are released into the medium following the lysis of the host cell. In the case of RGS34, such induction resulted in the production of TPs as well as normal phages (which arise by the excision of the plasmid DNA during the replication cycle). However, RGS34 was found to produce an exceptionally low number of normal phages, as measured by a plaquing assay. TPs are expected to be defective for plaque formation, since the presence of non-phage DNA prohibits them from carrying a full genome of phage DNA (the phages are limited in the amount of DNA that they can carry). Hence, a plaque-forming assay is not a direct measure of the number of TPs present, but only serves to provide a reference number to characterize the TP preparation. The RGS34 TP preparation contained $7 \times 10^4$ plaque forming units (pfu) per ml. In contrast, the induction of the normal P22 lysogen in the RGS11 progenitor strain would have produced about $1 \times 10^8$ pfu/ml.

DNA of RGS34-derived phages was prepared for its analysis as follows: 30 ml of RGS34 mitomycin-C-induced TPs were centrifuged at 72,000 g for 3 h. to pellet phages. The phage pellet was resuspended in 0.5 ml of TE buffer (10 nM tris-HCl, 1 mM Na$_2$EDTA, pH 8.0); phages were then treated with protease by the addition of Na$_2$EDTA, Sodium Dodecyl-Sulfate, and Proteinase-K to final concentrations of 20 mM, 0.5% and 50 ug/ml, respectively, followed by incubation at 37° C. for 1h. Following protease treatment, three phenol extractions and three ether extractions were done, then phage DNA was precipitated by the addition of ethanol to 66%. The purified phage DNA was dissolved in 100 ul of TE buffer. Restriction digests of RGS34 TP DNA were analyzed by gel electrophoresis, which showed the presence of extra bands (relative to normal P22 DNA) that corresponded with those expected from the incorporation of pRLG80 into the phage genome. This DNA analysis confirmed that TPs were in fact being produced by the RGS34 strain.

The RGS34 mitomycin-C-induced TP preparation initially contained bacterial cell debris which was pelleted by centrifugation at 4,000×g for 10 minutes (while leaving TPs still in suspension). However, much GUS activity was released during the lysis of TP-producing host cells, which remained in the TP suspension. Any GUS activity contained in the TP suspension would likely obscure the activity which resulted from transduction of the uidA gene, making it necessary to first purify the TP preparation prior to use. This was done by two successive rounds of centrifugation at 48,000 g to pellet the TPs, followed by resuspension of the TPs into fresh L-broth. This effectively diluted the GUS activity of the TP prep to a level near the background of the fluorescent GUS assay, described below.

The transduction assay was done by adding RGS34 TPs to exponential-phase cultures of bacteria, incubating several hours, then making an extract of the transduced cells which was assayed for GUS activity using the fluorescent substrate method. Cultures of *S. typhimurium* strain LT2 (a P22-sensitive strain) and *S. havana* (a P22-resistant strain of Salmonella) were grown at 37° C. to exponential phase, then adjusted (by dilution in fresh L-broth) to A$_{600}$=0.21 at the start of the experiment. Samples of sterile L-broth were included to allow the measurement of contaminating GUS activity added with the TP preparation, if any. To each 0.2 ml sample was added 0.1 ml of TP prep which contained $7 \times 10^3$ pfu total; a set of control samples was prepared similarly which, instead of TPs, received an equivalent amount of sterile LB. The samples were then incubated at 37° C. for 3.5 hours, after which the bacteria were pelleted by centrifugation and resuspended into 0.25 ml of GUS extraction buffer (50 mM Na-PO$_4$ pH 7.0, 1 mM Na$_2$EDTA, 0.1% Triton X-100, 10 mM B-mercaptoethanol). 5 ul of toluene was then added to each cell suspension (to permeabilize the cells allowing the release of the GUS enzyme into the extraction buffer), vortexed 40 seconds, then let stand at room temperature for 10 minutes. The samples were then centrifuged to pellet cell debris and separate phases, and 0.19 ml of each extract was removed to a fresh tube.

GUS assays were begun by adding 10 ul of a 20 mM solution of 4-methyl umbelliferyl glucuronide ("MUG"- the fluorescent substrate for GUS) to each 0.19 ml of cell extract. MUG itself is not fluorescent, but upon reaction with GUS releases the then-fluorescent 4-methyl umbelliferone group. Assays were incubated 30 minutes at 37° C., at which time 50 ul aliquots of each assay sample were removed and added to 0.95 ml of 0.2M $Na_2CO_3$ (the $Na_2CO_3$ stops the reaction and enhances the fluorescence of the reaction product). Fluorescence of the sample aliquots was then measured in a fluorescent spectrophotometer with excitation of the samples at 365 nm; fluorescent emissions were measured at 455 nm. The results are shown in Table 9.

TABLE 9

| Sample | Fluorescence Units |
| --- | --- |
| 1) LT2 Control | 45 |
| 2) LT2 + TPs | 1183 |
| 3) S. havana Control | 98 |
| 4) S. havana + TPs | 46 |
| 5) L broth Control | 38 |
| 6) L broth + TPs | 82 |

[1] Numbers indicate the fluorescence of samples measured with excitation at 365 nm and emission at 455 nm. Raw fluorescence units may be converted into the corresponding concentrations of 4-methyl unbellyferone (the fluorescent compound which is released by reaction of MUG with GUS), but serve here as relative measurements of GUS activity.

Table 9 shows that the only strongly positive reading of GUS activity occurred in the transduced LT2 sample (Sample 2). Since the residual GUS activity in the TP preparation (as determined by the difference between Samples 5 and 6) was negligible, the activity seen in Sample 2 was due to transduction. In contrast, the *S. havana* strain showed no increase in GUS activity due to exposure to the TPs. Thus, the GUS transduction system was shown to be operative for the $P22^s$ strain (LT2), but not for the $P22^r$ strain (*S. havana*). The background fluorescence measured in these samples was not likely the result of any intrinsic GUS activity in these strains (nor in sterile L-broth), but was probably due to the presence of small amounts of free 4-methyl umbelliferone in the MUG preparation.

Although the foregoing invention has been described in some detail by way of illustration and example for purposes of clarity of understanding, it will be obvious that certain changes and modifications may be practiced within the scope of the appended claims.

What is claimed is:

1. A method for specifically detecting viable target bacteria in a food sample, said method comprising:
    exposing bacteria in the food sample to a transducing particle specific for the target bacteria, said particle being capable of conferring transient expression of a screenable phenotype on the bacteria, wherein prior to exposure to the transducing particle the sample has been exposed to conditions selected to kill bacteria in the food sample; and
    detecting in a non-selected bacterial population from the sample the presence of only those bacteria which have survived the conditions to which they have been exposed and which express the screenable phenotype, wherein such expression indicates at least some target bacteria remain viable.

2. A method for specifically detecting viable target bacteria in a sterilized food sample, said method comprising:
    exposing the food sample to conditions selected to kill the target bacteria;
    thereafter incubating at least a portion of the food sample in the presence of a transducing particle specific for the target bacteria, said particle being capable of conferring transient expression of a screenable phenotype on the target bacteria; and
    detecting transient expression of the screenable phenotype in only those bacteria which have survived the conditions to which they have been exposed in the sample.

3. A method as in claim 1, wherein the sample has been exposed to heat which has debilitated the target bacteria.

4. A method as in claim 2, wherein the food sample has been exposed to heat in order to kill the bacteria.

5. A method as in claim 3 or 4, wherein the target bacteria are Salmonellae.

6. A method as in claims 1 or 2, wherein the screenable phenotype is visually detectable.

7. A method as in claim 6, wherein the screenable phenotype is ice nucleation activity.

8. A method as in claim 6, wherein the transducing particle carries an ice nucleation gene downstream from a promoter region.

9. A method as in claim 4, wherein the ice nucleation gene is selected from the group consisting of inaW, inaY, inaZ, and iceE.

10. A method as in claim 3, wherein the detectable phenotype is enzyme-catalyzed color production.

11. A method as in claim 7, wherein the color production is catalyzed by $\beta$ glucuronidase.

12. A method as in claims 1 or 2, wherein the sample is exposed to a plurality of transducing particles having different host range specificities, whereby the bacterial type may be determined based on the pattern of detectable phenotype conferred by said plurality of particles.

13. A method as in claims 1 or 2, wherein the sample is exposed to immobilized antibodies specific for the target bacteria prior to exposure to the transducing particle.

14. A method as in claims 1 or 2, wherein sample is selected from the group consisting of water, dairy products, and meat products.

15. A method as in claims 1 or 2, wherein the sample contains target bacteria and non-target bacteria and wherein said transducing particle is specific for the target bacteria but not for the non-target bacteria.

16. A method as in claims 1 or 2, wherein the transducing particle is derived from a bacteriophage selected from the group consisting of P22, L, ViI E15, E34, F0, 8, 23, 25, 31, 46, 98, 102, 163, and 175.

17. A method for specifically detecting viable target bacteria in a food sample, said method comprising:
    exposing bacteria in the sample to a transducing particle specific for the target bacteria, said particle being capable of conferring transient expression of ice nucleation activity on the target bacteria, wherein prior to exposure to the transducing particle the sample has been exposed to conditions selected to kill the target bacteria;
    incubating bacteria in the food sample under conditions which promote the formation of ice on only those bacterial cells which have survived the conditions to which they have been exposed and which express ice nucleation activity; and
    detecting ice formation in a non-selected bacterial population from the food sample, wherein ice formation is an indication that at least some target bacteria remain viable.

18. A method for specifically detecting viable target bacteria in a sterilized food sample, said method comprising:

exposing the food sample to conditions selected to kill the target bacteria;

thereafter incubating at least a portion of the food sample in the presence of a transducing particle specific for the target bacteria, said particle being capable of conferring transient,expression of ice nucleating activity on the target bacteria;

incubating the food sample under conditions which promote the formation of ice on bacterial cells which display ice nucleation activity; and detecting the ice formation in the sample.

19. A method as in claim 17, wherein the sample has been exposed to heat which has debilitated the target bacteria.

20. A method as in claim 18, wherein the food sample has been exposed to heat in order to kill the bacteria.

21. A method as in claim 18 or 19, wherein the target bacteria are Salmonellae.

22. A method as in claims 18 or 19, wherein the screenable phenotype is visually detectable.

23. A method as in claims 17 or 19, wherein the transducing particle carries an ice nucleation gene downstream from a promoter region.

24. A method as in claim 23, wherein the ice nucleation gene is selected from the group consisting of inaW, inaY, inaZ, and iceE.

25. A method as in claims 17 or 18, wherein the sample is exposed to a plurality of transducing particles having different host range specificities, whereby the bacterial type may be determined based on the pattern of detectable phenotype conferred by said plurality of particles.

26. A method as in claims 17 or 18, wherein the sample is exposed to immobilized antibodies specific for the target bacteria prior to exposure to the transducing particle.

27. A method as in claims 17 or 18, wherein sample is selected from the group consisting of water, dairy products, and meat products.

28. A method as in claims 17 or 18, wherein the sample contains target bacteria and non-target bacteria and wherein said transducing particle is specific for the target bacteria but not for the non-target bacteria.

29. A method as in claims 17 or 18, wherein the transducing particle is derived from a bacteriophage selected from the group consisting of P22, L, ViI, E15, E34, F0, 8, 23, 25, 31, 46, 98, 102, 163, and 175.

30. A method as in claim 18, wherein the food sample is incubated with the transducing particle in a growth medium at a temperature in the range from about 35° C. to 40° C. without agitation for a period from about 15 to 120 minutes.

31. A method as in claim 30, wherein the food sample is subsequently incubated at a temperature in the range from 20° C. to 25° C. for a period of from about 30 minutes to 2 hours to permit formation of ice nucleation sites.

32. A method as in claim 31, wherein the food sample is subsequently exposed to a temperature in the range from −3° C. to −12° C. to promote ice nucleation on cells possessing ice nucleation sites.

* * * * *